(12) United States Patent
Stevenson et al.

(10) Patent No.: US 7,770,456 B2
(45) Date of Patent: Aug. 10, 2010

(54) ELECTROMAGNETIC PIEZOELECTRIC ACOUSTIC SENSOR

(76) Inventors: Adrian Stevenson, Cambridge University Technical Services, Ltd., The Old Schools, Trinity Lane, Cambridge (GB) CB2 1TS; Christopher Robin Lowe, University of Cambridge, Tennis Court Road, Cambridge (GB) CB2 1QT ( * ) Notice: Subject to any disclaimer, the term of this patent is extended or adjusted under 35 U.S.C. 154(b) by 685 days.

(21) Appl. No.: 10/564,831

(22) PCT Filed: Jun. 4, 2004

(86) PCT No.: PCT/GB2004/002363
§ 371 (c)(1),
(2), (4) Date: Jan. 17, 2006

(87) PCT Pub. No.: WO2004/109272
PCT Pub. Date: Dec. 16, 2004

(65) Prior Publication Data
US 2006/0207330 A1 Sep. 21, 2006

(30) Foreign Application Priority Data
Jun. 4, 2003 (GB) .................................. 0312818.8

(51) Int. Cl.
*G01R 33/20* (2006.01)
*G01N 27/72* (2006.01)
(52) U.S. Cl. ............................. 73/632; 73/643; 73/644; 324/239
(58) Field of Classification Search ............... 73/632, 73/590, 643, 644, 1.44; 181/139; 324/239, 324/244
See application file for complete search history.

(56) References Cited

U.S. PATENT DOCUMENTS

| 3,248,595 | A | * | 4/1966 | Dehn | 315/5.16 |
| 3,599,196 | A | * | 8/1971 | Boyko | 340/552 |
| 3,663,858 | A | * | 5/1972 | Lisitano | 315/39 |
| 4,975,655 | A | * | 12/1990 | Dawson et al. | 359/240 |
| 6,196,059 | B1 | * | 3/2001 | Kosslinger et al. | 73/61.49 |
| 6,998,835 | B1 | * | 2/2006 | Brock et al. | 324/76.21 |
| 7,207,222 | B2 | * | 4/2007 | Thompson et al. | 73/590 |
| 7,216,054 | B1 | * | 5/2007 | Pchelnikov et al. | 702/150 |
| 2003/0011448 | A1 | * | 1/2003 | Pance | 333/219.1 |
| 2004/0217761 | A1 | * | 11/2004 | Wong et al. | 324/318 |

FOREIGN PATENT DOCUMENTS

WO 03019981 3/2003

* cited by examiner

*Primary Examiner*—J M Saint Surin
(74) *Attorney, Agent, or Firm*—Dykema Gossett PLLC

(57) ABSTRACT

An acoustic sensor comprises at least one resonant element. A driver comprises an electrical coupling means and an electromagnetic field source arranged such that the electrical coupling means transfers currents to the electromagnetic field source. The electromagnetic field source produces an electromagnetic field that drives the resonant elements to produce acoustic waves directed to a predetermined part of a test sample. Also provided is an electromagnetic detector for receiving the acoustic spectrum omitted from a test sample and an electrical circuit connected to the drive around detector.

33 Claims, 4 Drawing Sheets

FIGURE 3
6.6 MHZ
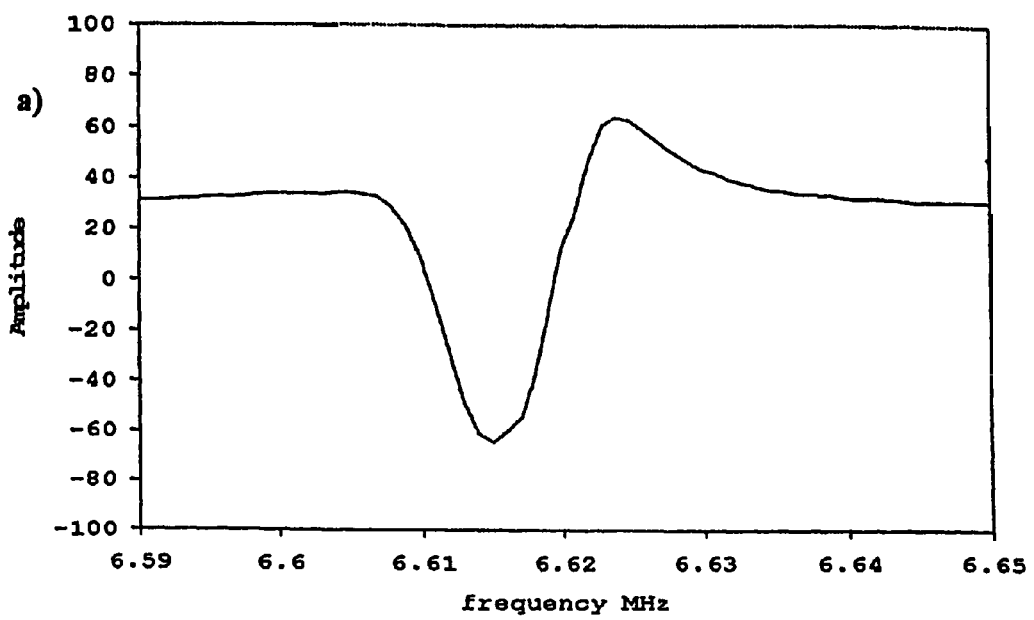
1.09 GHZ
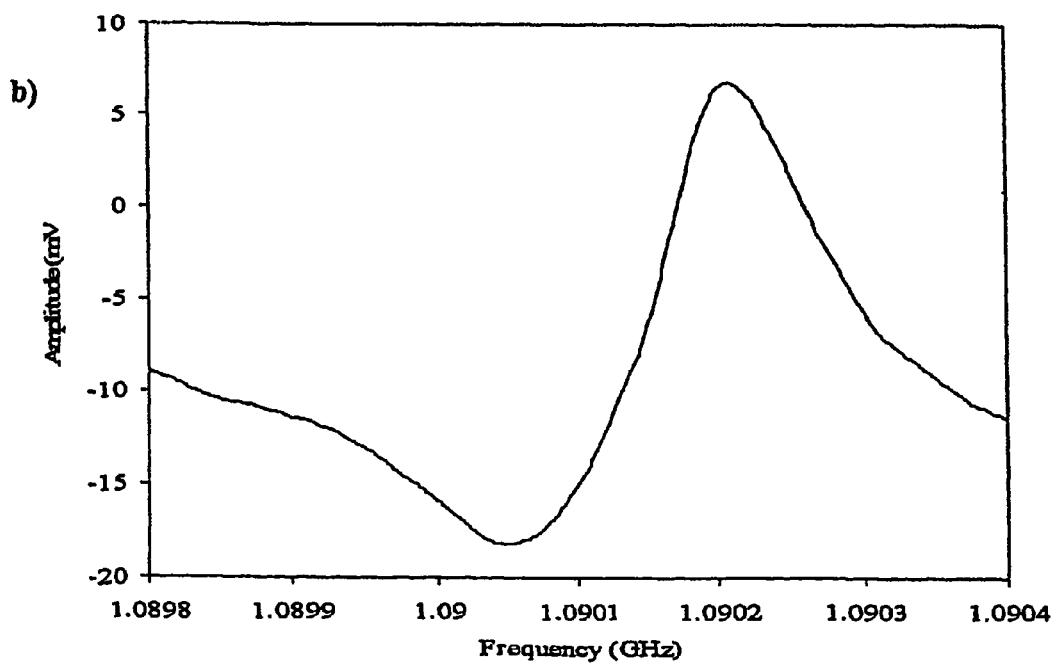

FIGURE 4
a)
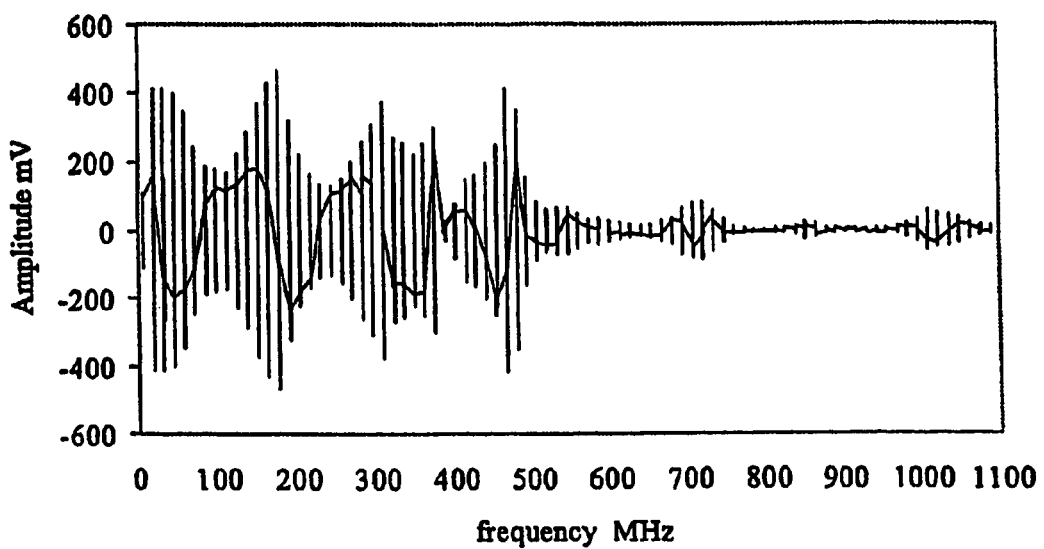
b)
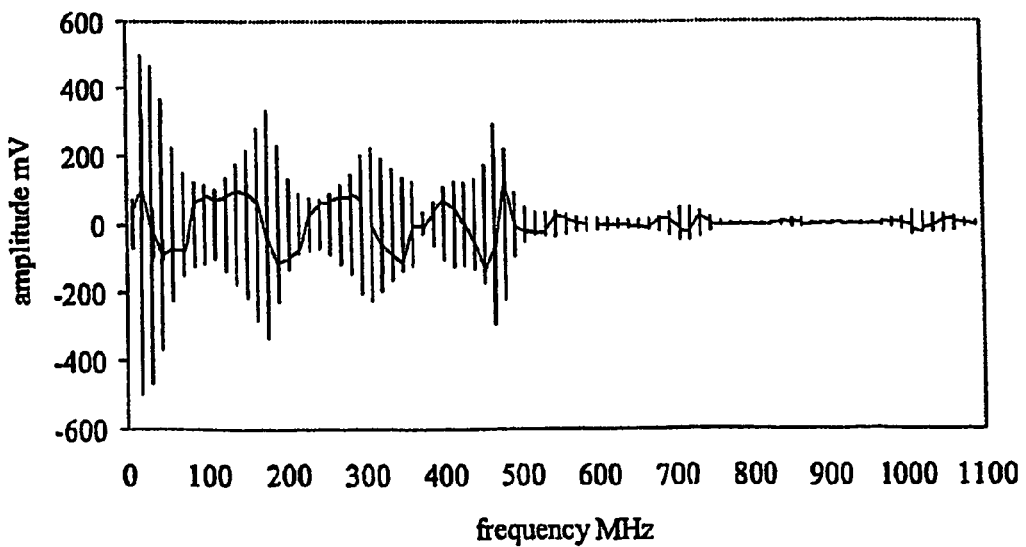

US 7,770,456 B2

ELECTROMAGNETIC PIEZOELECTRIC ACOUSTIC SENSOR

BACKGROUND OF THE INVENTION

1. Field of the Invention

Acoustic sensors which employ resonators have been used as detection devices for biological molecules for the past two decades, exhibiting sensitivity in the ng/ml range. They share with optical devices an ability to produce evanescent waves that propagate a limited distance across the solid liquid interface, so molecular events and processes in the bulk are not detected; only those processes leading to interfacial elasticity, viscosity, viscoelasticity and slippage are detected.

2. The Prior Art

However there are significant problems with these systems. As the dimensions of the molecules of interest range from 5 to 20 nm, a substantial amount (>95%) of acoustic transverse coupling is to the fluid above the chemical interface, essentially outside of the domain of the analysis in which there is interest.

An evanescent sensing region that is significantly thicker than the chemical layer of interest leads to reduced sensitivity and interpretation complications. For example, optical SPR (surface plasmon resonance) sensors generate a 200 nanometre evanescent wave, that is supposed to measure the refractive index of the protein layer, and yet it is the composite refractive index of the film and more significantly the fluid that is determined. Similarly electroded piezoelectric crystals known as TSMs (thickness shear mode) or QCMs (quartz crystal microbalances) operate at 10 MHz, which also have an evanescent penetration depth that reaches beyond the chemical layer of interest. Focusing the evanescent wave towards the interface has been attempted with magnetic acoustic resonance sensors that work at 50 MHz, however wave penetration still overshoots the interfacial chemistry with losses in sensitivity. Surface acoustic wave devices known as the Love wave device can work at higher frequencies for smaller penetration depths, however none of these systems provide a sufficiently compact evanescent zone to fully recover the biochemical signal.

A further restriction of these sensors is that a very limited window of information is recovered, at a single wavelength or frequency. This is tantamount to operating an IR spectrometer at a single wavelength, which severely reduces the value of the data recovered.

With respect to the practical format of these systems, all optical and acoustic devices require additional layers of metallisation to be applied and patterned, which for the interdigitated pattern on SAW (surface acoustic wave) is an especially costly process. In-use optical sensing systems require careful alignment and isolation from sources of vibration. Whilst the materials used in MARS (magnetic acoustic resonance sensor) and SAW are sensitive to temperature and demand careful environmental control in order to function without signal drifts. Wire connections to QSM and SAW devices are required, which reduces compatibility with chemical immobilisation modifications and procedures and places design constraints on commercial instruments.

The present invention aims to overcome the above limitations of conventional acoustic sensors.

SUMMARY OF THE INVENTION

According to the present invention there is provided an acoustic sensor comprising:
at least one resonant element;
a driver comprising an electrical coupling means and an electromagnetic field source, arranged such that, in use, the electrical coupling means transfers current to the electromagnetic field source to produce an electromagnetic field that drives the at least one resonant element to produce acoustic waves directed to a predetermined part of a test sample;

an electromagnetic detector arranged to receive, in use, the acoustic spectrum emitted from the test sample after the acoustic waves have interacted with the test sample; and an electrical circuit connected to the driver and electromagnetic detector, the circuit arranged, in use, to provide the current and to detect, in combination with the electromagnetic detector, the acoustic spectrum received by the electromagnetic detector.

According to the present invention there is also provided a method for use in acoustic sensing, the method comprising the steps of:

applying a current to an electrical coupling means;

transferring current from the electrical coupling means to an electromagnetic field source;

driving, with an electromagnetic field produced by the electromagnetic field source, at least one resonant element to produce acoustic waves to interrogate a test sample; and detecting with an electrical circuit connected to an electromagnetic detector and the electrical coupling means, the acoustic spectrum produced after the acoustic waves have interacted with the test sample.

An example of the present invention will now be described with reference to the accompanying drawings.

BRIEF DESCRIPTION OF THE DRAWINGS

FIG. 3a indicates the wide bandwidth of the system by showing the acoustic resonance envelope detected in the ultrasonic range for a quartz disc in contact with deionised water;

FIG. 3b indicates the wide bandwidth of the system by showing the acoustic resonance envelope detected in the hypersonic range for a quartz disc in contact with deionised water;

FIG. 4a shows the complete acoustic signal spectrum of a first example of 0.25 mm quartz disc in contact with deionised water, as measured with our described electrical system without any mechanical or electrical tuning of components;

FIG. 4b shows the complete acoustic signal spectrum of a second example of 0.25 mm quartz disc in contact with deionised water, as measured with our described electrical system without any mechanical or electrical tuning of components;

FIG. 5a shows the variation in acoustic Q factor;

FIG. 5b shows the operating frequency for a quartz disc in contact with deionised water; and FIG. 5c shows the evanescent waves depth for a quartz disc in contact with deionised water.

DETAILED DESCRIPTION OF THE PREFERRED EMBODIMENTS

Figure 1A:
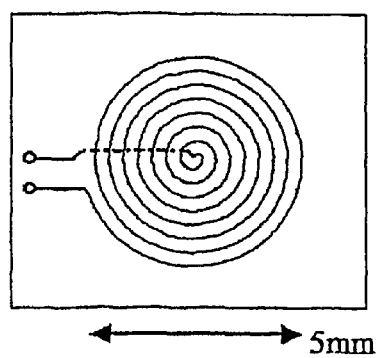
FIG. 1a shows an example spiral coil structure according to the present invention.
Figure 1B:
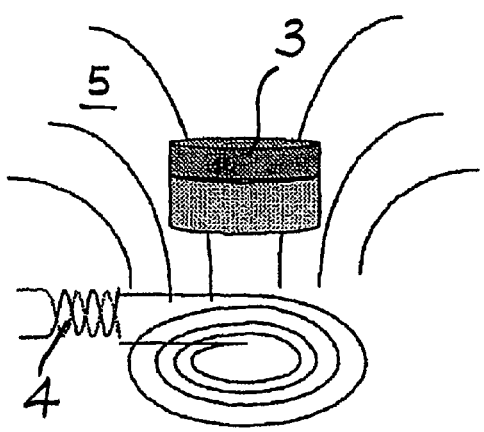
FIG. 1b shows an example coil and piezoelectric crystal according to the present invention, with electromagnetic field lines shown.
Figure 2:
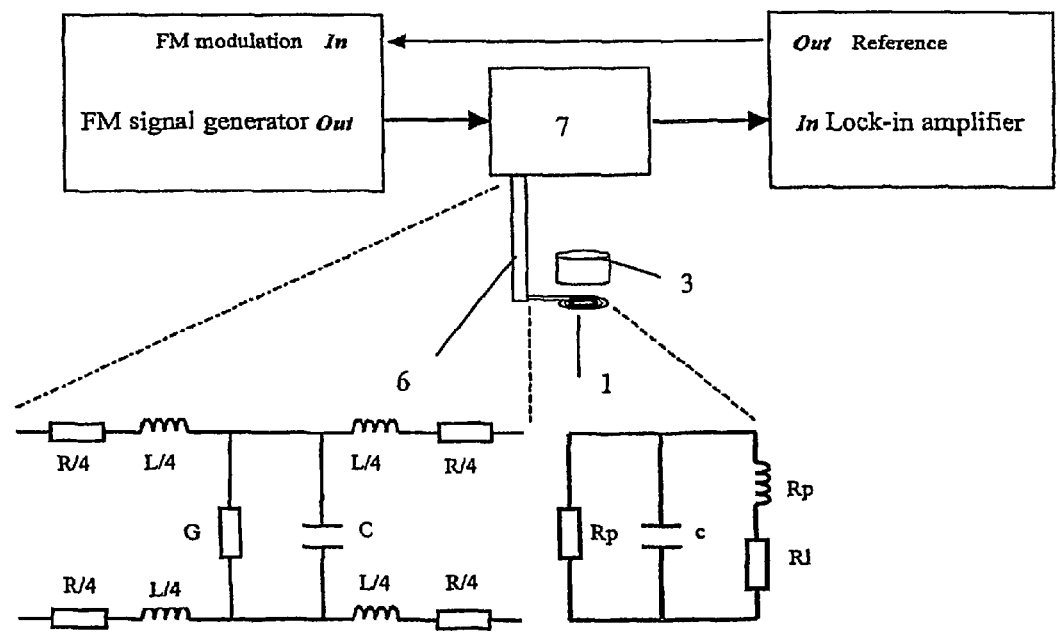
FIG. 2 shows an example based on a MARS signal generator and lock-in amplifier detector system used to generate and detect the acoustic signals according to the present invention and the electrical equivalent circuit of the coaxial cable and spiral coil.

FIG. 1b and FIG. 2 show an example arrangement in a sensor according to the present invention. A coil 1 receives RF current 4 via a multiply resonant transmission line 6. The electromagnetic field 5 produced by the coil 1 drives a piezoelectric element 3 to produce acoustic waves by electrostriction. The sensing done by the acoustic waves occurs either directly or indirectly. The substance to be detected either adsorbs to the vibrating surface, or a receptor can be attached to the vibrating surface, which is specific to the substance to be detected. When the substance adsorbs, it changes the acoustic spectrum. The coil 1 also acts as a detector which converts the changed electromagnetic field caused by the changed acoustic waves back into a RF current which is detected by a detection circuit, which includes an AM-diode detector 7 in this example.

The present invention eliminates the need for fine tuning between the transmission line 6 and the coil 1 in order to generate the desired acoustic waves, and acoustic waves which penetrate to the layer of interest can be produced. Also, acoustic waves with a wide range of frequencies can be produced.

The sensor can be used to detect substances such as cells, proteins antibodies and nucleic acids.

We have identified that the problem of low frequency of operation of current acoustic resonant devices is not to do with the material, but with how the material is excited.

The opportunity to focus evanescent waves substantially to the chemical interface, and enhance molecular coupling, is exemplified by the low intrinsic loss of amorphous glasses and single crystal materials, which supports operation at GHz frequencies.

In terms of coupling processes that have been used to date to excite magnetic films and piezoelectric crystals, the presence of the sample in the electromagnetic field to excite acoustic waves/phonons has been sufficient to achieve generation in the hypersonic GHz range. In contrast, known acoustic sensor configurations rely on electrical signals transmitted through wires to metal electrodes in order to excite the acoustics. This has continued with surface acoustic waves devices, which obtain higher frequencies of operation, but these are still inconvenient for locating hypersonic transverse waves that can concentrate at the molecular interface. This coupling limitation of the electrode to low frequencies, has been addressed in the present invention by providing an alternating electric or magnetic dipole constructed, for example, from a spiral coil 1, that has many attractive measurement properties. Alternatively, the coil 1 could be replaced by a linear electric dipole and the same function achieved at a different signal to noise ratio. A primary advantage is ultrasonic generation in a wide variety of substrates and composites that include metals, glasses, sapphire, diamond, silicon, quartz, lithium niobate, lithium tantalate, and nickel, simply by placing the substrate material above the coil. For substrates of low intrinsic loss such as amorphous and single crystal resonators, piezoelectricity, magnetostriction and magnetic direct generation can be used to initiate coupling at different frequencies, in order to provide new molecular information from transverse wave coupling at the solid-liquid interface. The only substrate materials that cannot be acoustically excited with a coil are insulators which do not incorporate any magnetic or electric dipoles or any conductive region. Therefore the resonant element 3 can be made of one of a wide range of materials or a combination of several. It can be any material with magnetic or electric dipoles that acquires energy from the electrical or magnetic components of the radio frequency electromagnetic waves and translates that acquired energy into acoustic motion, preferably as a standing wave in the material.

The present invention is the result of optimising the electrical configuration so coupling between the dipoles instigated in an electromagnetic source such the spiral coil 1 and dipoles in a material element lead to wideband ultrasonic and hypersonic evanescent wave generation. We have determined that the electrical circuit components are very important in enabling or restricting the flow of RF current to the coil, so fluctuations in the magnitude of these currents due to the acoustic generation process can be measured.

In order to generate hypersonic evanescent waves an examination of the electrical impedance of the components that will transfer current from the signal generator to the spiral coil antenna is important. The strategy used in the invention is to take the MARS system which has already been developed for spiral coil operation, and improve it so that there is no need for mechanical tuning. In the prior art, a capacitor mounted alongside the coil is used to establish electrical parallel resonance, which not only requires significant time to match the electrical and acoustic resonance frequencies, but also tends to quench the resonance due to dielectric loss in the capacitor. The present invention avoids this by the tuning capacitor being dispensed with entirely, relying on the characteristics of a transmission cable 6 between the coil and the signal source. At these high frequencies each connection that would be ignored at lower MHz frequencies now becomes an important component of the signal-to-noise ratio of the system.

The preferred embodiment of the present invention uses a MARS system with a sensitive detection circuit that uses a differential amplifier and synchronous receiver to recover acoustic signals without contacting the vibrating elements, although any means that can generate radio frequency currents and detect them in the MHZ to GHZ range can be used. In this embodiment, the coil carries out the electromagnetic detection function as well as the electromagnetic field source function. This does not have to be the case. The electromagnetic field source and detector can be two different elements. The differential amplifier operates to increase the received signal, and at the same time, subtract away the unwanted transmitted signal, whilst the synchronous receiver follows on by eliminating external noise through a process of very narrow bandwidth filtering, so high signal-to-noise ratios can be recovered from the sensing device.

In an example of the present invention, AT cut 6 MHz 0-25 mm piezoelectric crystals are contained in a flow through cell into which a spiral coil 1 element had been incorporated. An E8254A signal generator (40 GHz) is used to supply a frequency modulated RF signal 4 to the coil 1, whilst an in-house differential AM detector 7 and the EG&G lock-in amplifier extract the acoustic signal. See FIG. 1. The coil 1 is on a supporting epoxy laminate board 2. All of the harmonic frequencies of the crystal are collected by continuously scanning the resonance amplitudes from 6 MHz to 1.1 Ghz over precisely defined frequency intervals. An HP impedance analyser with a 16992A test set is used to characterise the electrical impedance of the coil and transmission line, so the acoustic response can be interpreted. Directly using an impedance analyser is an alternative to a modified MARS system.

As the MARS system operates at several different harmonic frequencies, the electrical conditions and their contribution at the different frequencies to current through the coil are very important to system behaviour, particularly to the signal-to-noise ratio at hypersonic frequencies. For this reason the calculated and measured electrical impedance of the coil and the transmission line are used as a backcloth from which to interpret the acoustic data.

Although a coil is used in this embodiment, the electromagnetic field source can be other inductors or means to produce a radio frequency electromagnetic waves from a radio frequency current, such as a single wire or a microwave horn. Similarly, a transmission line is not the only possible electrical coupling means that could be used. It could be any hard wire connection that links the electromagnetic field source to the electrical circuit and induces standing waves.

As shown in FIG. 1, the spiral coil 1 is used to induce an RF electrical field 5 in a piezoelectric plate 3, and can be described by an equivalent circuit of impedance $Z_R$ $$Z_R = \left(j\omega c + \frac{1}{R_L + j\omega l} + \frac{1}{R_p}\right)^{-1}$$

comprising a capacitor (1.7 pF), inductor (1.15 uH) a wire, resistance (5 Ohm) and parallel resistance (8000 Ohm) as indicated in FIG. 2. For a 30 turn coil made from 0.085 mm enamelled copper wire, a precise fit between the calculated and experimental response, determined via the HP impedance analyser (4291B), can be obtained. A comparison with an electroded TSM 6.5 MHz device indicates the large difference in impedance between capacitive and inductively coupled crystals, indicating that electrical conditions for acoustic detection will necessarily be different in these two cases. One key difference understood from the equivalent circuits is that the coil exhibits a parallel electrical resonance (matching resonance), even when no capacitance is directly attached to the coil. This behaviour is due to inter winding and substrate capacitance, which may shunt valuable current away from driving of the acoustic resonance and contribute to dielectric losses at hypersonic frequencies. However, as quick recovery of data over a wide bandwidth is desirable, time consuming manual tuning of the electrical characteristic is avoided by using a multiply resonant coaxial transmission line, 6, or other electrical coupling means, between the coil and detector.

Because of its repeating electrical impedance, the coaxial line 6 transfers RF current over a wide bandwidth without deleterious matching losses. For this reason, it effectively replaces the capacitor used with the original MARS system, which acts as a current shunt at high frequency. The impedance of the transmission line 6 can be calculated from Z.

$$Z = Z_0 \left[\frac{(Z_R/Z_0) + \operatorname{Tanh}[yd]}{1 + (Z_R/Z_0)\operatorname{Tanh}[yd]}\right]$$

where $\gamma = \sqrt{(R+j\omega l)(G+j\omega C)}$ and $Z_0 = \sqrt{(R+j\omega L)/(G+j\omega C)}$, where $\gamma=\sqrt{(R+j\omega l)(G+j\omega C)}$ and $Z_0=\sqrt{(R+j\omega L)/(G+j\omega C)}$, and d is the length of the line 6 and shown to fit our experimental data when R=0.1 ohm, L=0.23 uH, C=55 pF and G=$10^{-9}$. Its repeat behaviour is. due to the electromagnetic standing wave condition in the line, which leads to multiple resonances similar to acoustic resonance, however, the lower electrical Q factor leads to impedance fluctuations of the line staying within a specified range. This prevents severely mis-matched electrical conditions from arising, whilst retaining simplicity without the need for manual tuning. These coaxial line resonances therefore assist acoustic detection at very high frequencies.

Current transferred to the coil 1 due to the combined response of the coil 1 and coaxial line 6 can be calculated by adding the real and imaginary parts of the coil and line impedance together, to give the overall impedance connected to the detector. To predict the acoustic behaviour with frequency, it is necessary to use the impedance formula for the coil to determine the consequence of a radiation resistance, that appears at the acoustic resonance frequency. This resistance is in series with the wire resistance and describes the loss of power to the acoustic resonance. Assuming the radiation resistance due to the acoustic generation is constant with frequency, it can be demonstrated that the acoustic response appears as measurable fluctuations in the electrical impedance.

The basis to acoustic generation is the electrical current following through the coil and the transmission line and its interaction with the magnetic or electric dipoles in the disk. Here, current driven through the electrical network to the coil 1 leads to a varying magnetic field (Ampere's law) and in turn and electrical field 5 (Faraday's law) which forces dipoles into motion. In the example presented here, this process is the dipoles in the piezoelectric disc 3 being driven by an electric field via electrostriction, effectively a change in dimension of the disc within the field. For acoustic generation across many frequencies, the following conditions must be satisfied: (1) sufficient current must be available in the windings of the spiral coil (2) the resulting electrical fields must be predominantly perpendicular to the plane of the disk (AT piezoelectric crystal only) (3) the acoustic loss needs to be minimal. Placing energy in the acoustic spectrum is critically dependent on the coil construction, and the highest frequency of generation desired.

As indicated above, acoustic generation at hypersonic frequencies depends on satisfying key criteria, which we, now relate to our measured acoustic response (FIG. 5) detected with the FM signal generator and AM detector, lock in amplifier receiver (FIG. 2).

A simple acoustic amplitude is not measured but the differential of the amplitude with respect to frequency (FIG. 5). This behaviour arises as the changes in the frequency of the signal via FM modulation produces a low noise AM signal only if the electrical impedance fluctuates rapidly with frequency: a situation brought about by any high Q acoustic resonance, ($10^3$-$10^4$). So overall, the differential of the acoustic amplitude with frequency is what is being detected, for the reason that much higher signal-to-noise ratios of >3000 up to 600 MHz can be achieved than by directly measuring the amplitude. For example in the alternative measurement format where direct connection is made between the coil and the impendance analyser, then resolution of many of the resonance envelopes is not possible due to low signal-to-noise conditions, however improved coil construction may make this option a useful approach. As frequency is a fundamental determinant of the response, the spectrum contains a lot of information about to the behaviour of the system and how the electrical network can lead on to hypersonic operation.

Each of the resonances in FIG. 5 fits precisely to anticipated shear wave resonance frequencies, as a precise frequency interval of 13.21380 MHz is measurable across the series. The velocity calculated from this value is 3750 ms$^{-1}$, which is the shear wave velocity of an AT crystal, which shows the acoustic shear wave harmonics are being detected by the MARS system.

Beyond N=61, a periodicity in the envelope of the peak amplitude becomes obvious. This is related simply to the length of the coaxial line.

As can be seen from FIG. 5, the vertical bars are all separated by exactly the same frequency, indicating that the shear harmonic mode is what is being collected. However this incremental behaviour does not cease, but continues throughout the trace to a lift in the resonance envelope at 1.0902 GHz. This shows that hypersonic signals are being generated.

Figure 6:
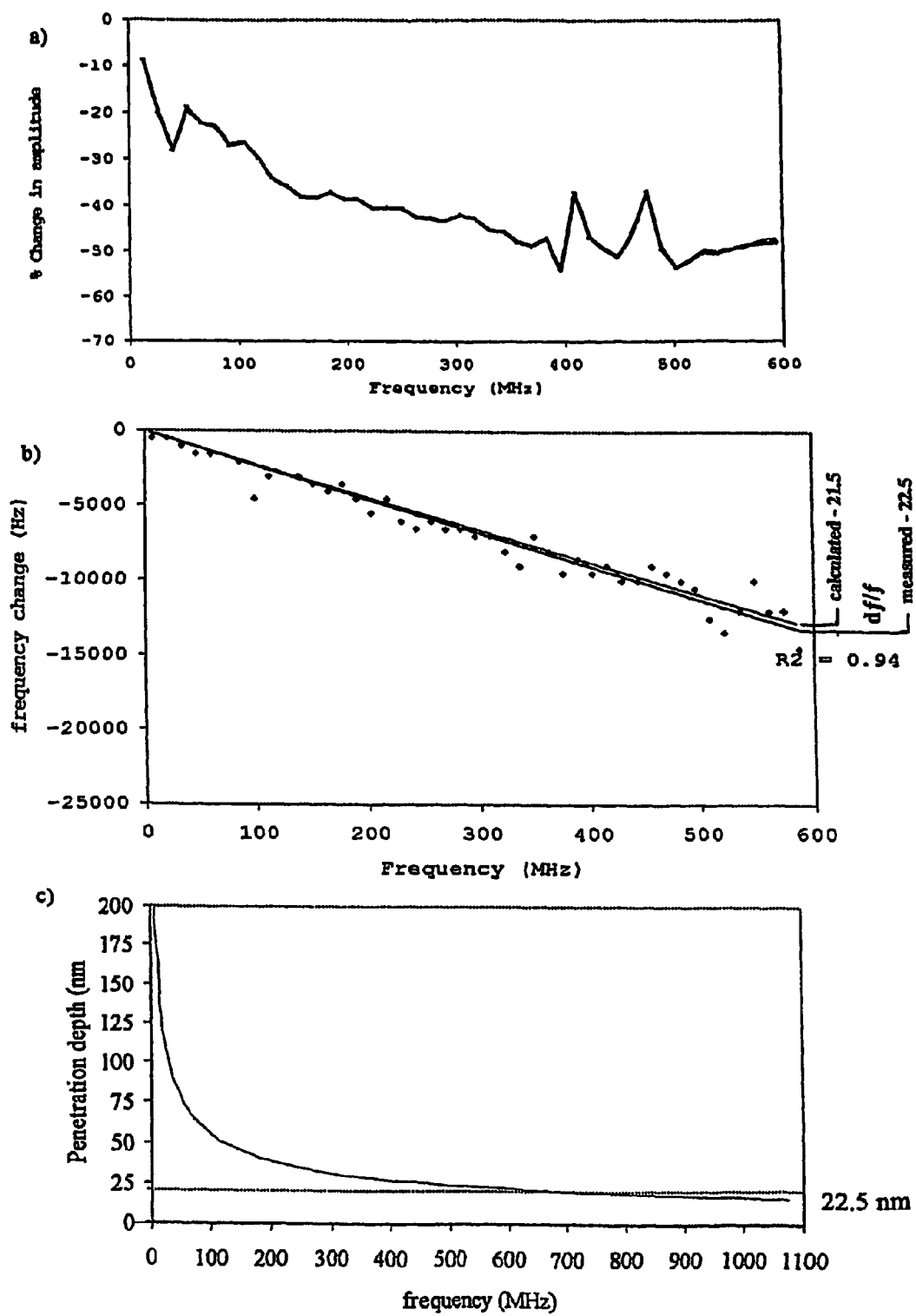

On selecting harmonic No. 165, a smooth resonance contour was found that does not have the regular and harmonic responses associated with non plane parallel surfaces. The fact that an acoustic resonance had been detected was supported by the measured Q factor, which was consistent with the rest of the family of shear wave resonances observed. As further confirmation that acoustic harmonic signals are being monitored over multiple frequencies where evanescent wave depth decreases with frequency, a solution of IgS was injected at 1000 µg/ml. FIG. 6 shows that the frequency a) and amplitude b) is shifted in a frequency dependent manner. FIG. 6c) shows how the frequencies relate to the evanescent penetration depth.

An effective method for ultrasonic and hypersonic generation at the solid liquid interface without mechanical tuning has been demonstrated, with acoustic losses consistent with superior coupling to a chemical recognition layer, and less radiation into the overlying supernatent. This process uses simple system components, such as a hand wound coil, lock-in amplifier and signal generator. For sensing applications many different chemical recognition systems can be immobilised on the sensing element involving antibodies, cells, nucleic acids and the acoustic fingerprint or spectra used to extract changes in conformation and composition of a nanoscale film. The ability to select different operating frequencies with this approach, can be used to explore ultrasonic and extended hypersonic changes in surface stress, relaxation, and slippage of a nanoscale film to provide a new tool for drug discovery and clinical diagnostics.

The invention claimed is:

1. An acoustic sensor comprising:
   at least one resonant element;
   a driver comprising an electrical coupling means and an electromagnetic field source, arranged such that, in use, the electrical coupling means transfers current to the electromagnetic field source which produces an electromagnetic field that wirelessly drives the at least one resonant element, with matching resonances of the electromagnetic field source and the at least one resonance element, to produce acoustic waves directed to a predetermined part of a test sample, said electrical coupling means comprising a multiply resonant coaxial transmission line;
   an electromagnetic detector arranged to receive, in use, the acoustic spectrum emitted from the test sample after the acoustic waves have interacted with the test sample; and
   an electrical circuit connected to the driver and electromagnetic detector, the circuit arranged, in use, to provide the current and to detect, in combination with the electromagnetic detector, the acoustic spectrum received by the electromagnetic detector.

2. The sensor according to claim 1, wherein the electrical circuit comprises an electrical oscillator.

3. The sensor according to claim 1, wherein the electrical circuit comprises a frequency modulated signal generator, an AM diode detector and a lock-in amplifier.

4. The sensor according to claim 1, wherein the electromagnetic field source and the electromagnetic detector are the same member.

5. The sensor according to claim 1, wherein the electromagnetic field source is a single wire.

6. The sensor according to claim 4, wherein the electromagnetic field source is a coil.

7. The sensor according to claim 6, wherein the coil is spiral.

8. The sensor according to claim 7, wherein the coil is copper.

9. The sensor according to claim 8, wherein the coil is formed from wire wound into a flat spiral element.

10. The sensor according to claim 4, wherein the electromagnetic field source is a microwave horn.

11. The sensor according to claim 10, wherein the electromagnetic detector is a single wire.

12. The sensor according to claim 10, wherein the electromagnetic detector is a coil.

13. The sensor according to claim 12, wherein the coil is spiral.

14. The sensor according to claim 13, wherein the coil is copper.

15. The sensor according to 14, wherein the coil is formed from wire wound into flat spiral element.

16. The sensor according to claim 10, wherein the electromagnetic detector is a microwave horn.

17. The sensor according to claim 16, wherein the resonant element is metal.

18. The sensor according to claim 17, wherein the resonant element is magnetostrictive.

19. The sensor according to claim 16, wherein the resonant element is piezoelectric.

20. The sensor according to claim 19, wherein the resonant element is a composite of at least two different materials.

21. The sensor according to claim 20, wherein the test sample is in a gaseous phase.

22. The sensor according to claim 21, wherein the resonant element is coated with a polymer layer.

23. The sensor according to claim 22, wherein the test sample is in a liquid phase.

24. The sensor according to claim 23, wherein the resonant element is coated with a biorecognition layer.

25. The sensor according to claim 24, wherein in use, the sensor detects cells.

26. The sensor according to claim 24, wherein in use, the sensor detects proteins.

27. The sensor according to claim 24, wherein in use, the sensor detects antibodies.

28. The sensor according to claim 24, wherein in use, the sensor detects nucleic acids.

29. A method for use in acoustic sensing, the method comprising the steps of:
   applying a current to a multiply resonant coaxial transmission line;
   transferring current from the multiply resonant coaxial transmission line to an electromagnetic field source;
   wirelessly driving, with an electromagnetic field produced by the electromagnetic field source, at least one resonant element to produce acoustic waves directed to a predetermined part of a test sample, resonances of the electromagnetic field being matched with resonance of said acoustic waves; and detecting with an electrical circuit connected to the electromagnetic field source together with an electromagnetic detector and the electrical coupling means, an acoustic spectrum produced after the acoustic waves have interacted with the test sample.

30. The method according to claim 29, wherein the at least one resonant element produces acoustic waves by electrostriction.

31. The method according to claim 29, wherein the at least one resonant element produces acoustic waves by magnetostriction.

32. The method according to claim 31, wherein the acoustic waves are detected by means of an electrical oscillator tuned to the fundamental or harmonic frequency of the resonant element.

33. The method according to claim 31, wherein the acoustic waves are detected by means of a frequency modulated signal generator, an AM diode detector and a lock-in amplifier.

* * * * *